US 8,600,507 B2

(12) United States Patent
Brase et al.

(10) Patent No.: US 8,600,507 B2
(45) Date of Patent: Dec. 3, 2013

(54) MULTI-PORT MODULAR CONNECTOR FOR IMPLANTABLE ELECTRICAL STIMULATION SYSTEMS AND METHODS OF MAKING AND USING

(75) Inventors: Randall Lee Brase, Castaic, CA (US); Robert Randall Tong, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 754 days.

(21) Appl. No.: 12/506,532

(22) Filed: Jul. 21, 2009

(65) Prior Publication Data

US 2011/0022100 A1    Jan. 27, 2011

(51) Int. Cl.
*A61N 1/08* (2006.01)

(52) U.S. Cl.
USPC .................... 607/36; 439/668; 439/717

(58) Field of Classification Search
USPC .................... 439/668, 717; 607/36–38
See application file for complete search history.

(56) References Cited

U.S. PATENT DOCUMENTS

| | | | |
|---|---|---|---|
| 3,908,668 A | 9/1975 | Bolduc | |
| 3,951,154 A | 4/1976 | Hartlaub | |
| 4,832,032 A | 5/1989 | Schneider | |
| 5,374,279 A | 12/1994 | Duffin, Jr. et al. | |
| 6,167,314 A | 12/2000 | Fischer, Sr. et al. | |
| 6,181,969 B1 | 1/2001 | Gord | |
| 6,516,227 B1 | 2/2003 | Meadows et al. | |
| 6,609,029 B1 | 8/2003 | Mann et al. | |
| 6,609,032 B1 | 8/2003 | Woods et al. | |
| 6,662,035 B2 | 12/2003 | Sochor | |
| 6,741,892 B1 | 5/2004 | Meadows et al. | |
| 6,757,039 B2 | 6/2004 | Ma | |
| 6,878,013 B1 | 4/2005 | Behan | |
| 6,895,276 B2 | 5/2005 | Kast et al. | |
| 7,128,600 B2 | 10/2006 | Osypka | |
| 7,225,034 B2 | 5/2007 | Ries et al. | |
| 7,242,987 B2 | 7/2007 | Holleman et al. | |
| 7,244,150 B1 | 7/2007 | Brase et al. | |

(Continued)

FOREIGN PATENT DOCUMENTS

| | | |
|---|---|---|
| EP | 1479133 B1 | 11/2004 |
| WO | 03035173 A1 | 5/2003 |

(Continued)

OTHER PUBLICATIONS

U.S. Appl. No. 11/238,240, filed Sep. 29, 2005, 20 pgs.

(Continued)

*Primary Examiner* — Brian T Gedeon
(74) *Attorney, Agent, or Firm* — Frommer Lawrence & Haug LLP; Patrick R. Turner (57) ABSTRACT

A connector for an electrical stimulation system includes an assembly of individual contact modules arranged along a common axis. Each contact module includes a body having a seat and at least two insertion apertures. An aperture contact is associated with each of the insertion apertures and is configured and arranged to electrically couple to a terminal of an elongated member when the elongated member is inserted into the associated insertion aperture. A seal plate is disposed in each seat of an associated one of the contact modules such that the seal plate is sandwiched between adjacent contact modules. Each seal plate is configured and arranged to electrically isolate the aperture contacts of the associated contact module from the aperture contacts of the other contact modules.

20 Claims, 10 Drawing Sheets

(56) References Cited

U.S. PATENT DOCUMENTS

| | | |
|---|---|---|
| 7,270,568 B2 | 9/2007 | Osypka |
| 7,422,487 B2 | 9/2008 | Osypka |
| 7,554,493 B1 | 6/2009 | Rahman |
| 7,585,190 B2 | 9/2009 | Osypka |
| 2003/0050549 A1 | 3/2003 | Sochor |
| 2003/0077943 A1 | 4/2003 | Osypka |
| 2003/0114905 A1 | 6/2003 | Kuzma |
| 2003/0163171 A1 | 8/2003 | Kast et al. |
| 2003/0231266 A1 | 12/2003 | Ma |
| 2004/0059392 A1 | 3/2004 | Parramon et al. |
| 2004/0064164 A1 | 4/2004 | Ries et al. |
| 2004/0230268 A1 | 11/2004 | Huff et al. |
| 2004/0260355 A1 | 12/2004 | Holleman et al. |
| 2004/0260373 A1 | 12/2004 | Ries et al. |
| 2005/0027326 A1 | 2/2005 | Ries et al. |
| 2005/0043770 A1 | 2/2005 | Hine et al. |
| 2005/0043771 A1 | 2/2005 | Sommer et al. |
| 2005/0165465 A1 | 7/2005 | Pianca et al. |
| 2005/0186829 A1 | 8/2005 | Balsells |
| 2005/0272280 A1 | 12/2005 | Osypka |
| 2006/0015163 A1 | 1/2006 | Brown |
| 2006/0166563 A1 | 7/2006 | Osypka |
| 2006/0167522 A1 | 7/2006 | Malinowski |
| 2006/0259106 A1 | 11/2006 | Arnholt et al. |
| 2007/0099487 A1 | 5/2007 | Osypka |
| 2007/0150007 A1 | 6/2007 | Anderson et al. |
| 2007/0150036 A1 | 6/2007 | Anderson |
| 2007/0161294 A1 | 7/2007 | Brase et al. |
| 2007/0219595 A1 | 9/2007 | He |
| 2007/0239243 A1 | 10/2007 | Moffitt et al. |
| 2008/0071320 A1 | 3/2008 | Brase |
| 2008/0139031 A1 | 6/2008 | Ries et al. |
| 2008/0177167 A1 | 7/2008 | Janzig et al. |
| 2008/0208277 A1 | 8/2008 | Janzig et al. |
| 2008/0208278 A1 | 8/2008 | Janzig et al. |
| 2008/0208279 A1 | 8/2008 | Janzig et al. |
| 2008/0274651 A1* | 11/2008 | Boyd et al. .............. 439/717 |
| 2008/0311772 A1 | 12/2008 | Osypka |
| 2009/0233491 A1 | 9/2009 | Barker et al. |
| 2009/0264943 A1 | 10/2009 | Barker |

FOREIGN PATENT DOCUMENTS

| | | |
|---|---|---|
| WO | 03075414 A1 | 9/2003 |
| WO | 2004030758 A1 | 4/2004 |
| WO | 2004112899 A2 | 12/2004 |
| WO | 2005009534 A1 | 2/2005 |
| WO | 2005023364 A1 | 3/2005 |
| WO | 2005025009 A1 | 3/2005 |
| WO | 2008088565 A1 | 7/2008 |
| WO | 2008088566 A1 | 7/2008 |
| WO | 2008088567 A1 | 7/2008 |
| WO | 2008088568 A1 | 7/2008 |
| WO | 2009045772 A1 | 4/2009 |
| WO | 2009045809 A2 | 4/2009 |

OTHER PUBLICATIONS

International Patent Application No. PCT/US2010/041793 filed Jul. 13, 2010, International Search Report and Written Opinion mailed Oct. 19, 2010.

* cited by examiner

MULTI-PORT MODULAR CONNECTOR FOR IMPLANTABLE ELECTRICAL STIMULATION SYSTEMS AND METHODS OF MAKING AND USING

FIELD

The present invention is directed to the area of implantable electrical stimulation systems and methods of making and using the systems. The present invention is also directed to implantable electrical stimulation leads having a modular connector with multiple ports, as well as methods of making and using the connectors and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Deep brain stimulation has also been useful for treating refractory chronic pain syndromes and has been applied to treat movement disorders and epilepsy. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Moreover, electrical stimulation systems can be implanted subcutaneously to stimulate subcutaneous tissue including subcutaneous nerves such as the occipital nerve.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In one embodiment, a connector for an electrical stimulation system includes an assembly of individual contact modules arranged along a common axis. The assembly has a first end and a second end. Each contact module includes a body having a first major surface and an opposing second major surface. The first major surface defines a seat and at least two insertion apertures. The body includes at least two aperture contacts. Each aperture contact is associated with one of the insertion apertures and is configured and arranged to electrically couple to a terminal of an elongated member when the elongated member is inserted into the associated insertion aperture. A first end plate is positioned at the first end of the assembly of individual contact modules. The connector also includes a plurality of seal plates. A different one of the seal plates is disposed in each seat of an associated one of the contact modules such that the seal plate is sandwiched between the associated contact module and one other contact module of the assembly or the first end plate. Each seal plate is configured and arranged to electrically isolate the aperture contacts of the associated contact module from the aperture contacts of the other contact modules. A second end plate is positioned at the second end of the assembly of individual contact modules. The second end plate is coupled to the first end plate by a retaining mechanism and configured and arranged to facilitate arrangement of the assembly along the common axis.

In another embodiment, a connector for an electrical stimulation system includes an assembly of individual contact modules arranged along a common axis. The assembly has a first end and a second end. Each contact module includes a body defining at least two insertion apertures. For each of the at least two insertion apertures, an aperture contact is disposed in the body and exposed in the corresponding insertion aperture. The aperture contact is configured and arranged to electrically couple to a terminal of an elongated member when the elongated member is inserted into a corresponding one of the at least two insertion apertures. A first end plate is positioned at the first end of the assembly of individual contact modules. The first end plate defines at least two insertion apertures. The insertion apertures of the first end plate are configured and arranged to align with the insertion apertures of each of the contact modules. The connector further includes a plurality of seal plates. Each seal plate is coupled to the body of one of the contact modules such that each seal plate is sandwiched between the contact module onto which the seal plate is coupled and one of another contact module of the assembly or the first end plate. The seal plate defines at least two insertion apertures. Each seal plate is configured and arranged to electrically isolate each of the aperture contacts from other aperture contacts in an adjacent contact module. A second end plate is positioned at the second end of the assembly of individual contact modules.

In yet another embodiment, a method for forming a connector includes inserting a seal plate into a seat defined in a contact module for each of a plurality of contact modules. The contact module defines at least two insertion apertures. The seal plate defines at least two insertion apertures aligned with the at least two insertion apertures defined in each contact module. The seal plate includes at least one seal disposed around each insertion aperture defined in the seal plate. The contact module includes an aperture contact configured and arranged to electrically couple with a terminal of an elongated member when the elongated member is inserted in the insertion aperture. The plurality of contact modules and coupled seal plates are aligned along an axis so that the insertion apertures of the plurality of contact modules are aligned. The plurality of contact modules are retained between a first end cap at a first end of the aligned plurality of contact modules and a second end cap at a second end of the aligned plurality of contact modules. The first end cap defines at least two insertion apertures aligned with the at least two insertion apertures defined in each contact module thereby forming at least two ports configured and arranged to receive an elongated member with spaced-apart terminals.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation leads having a modular connector with multiple ports, as well as methods of making and using the connectors and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; and 6,741,892; and U.S. patent application Ser. Nos. 10/353,101, 10/503,281, 11/238,240; 11/319,291; 11/327,880; 11/375,638; 11/393,991; and 11/396,309, all of which are incorporated herein by reference.

Figure 1:
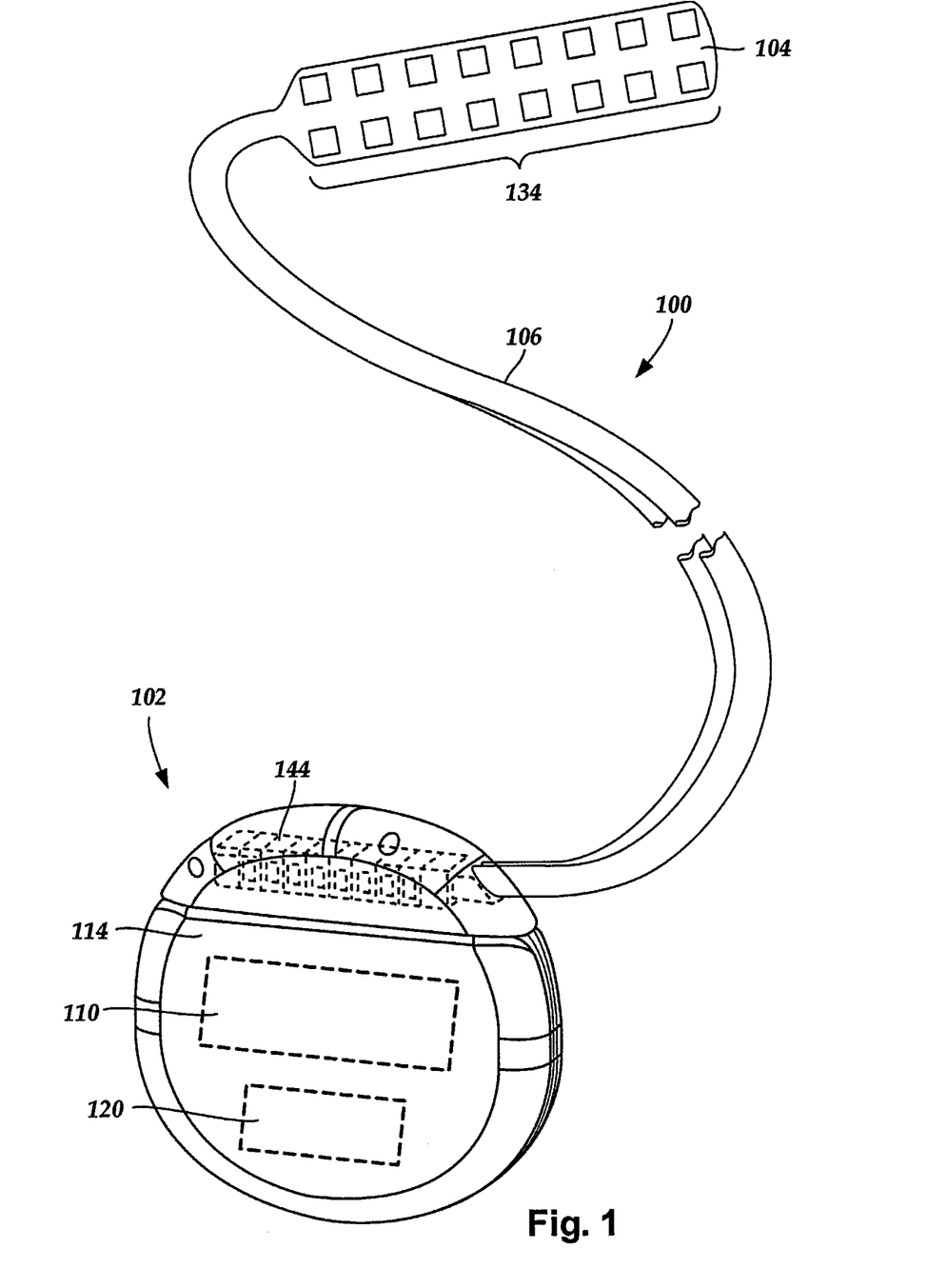
FIG. 1 is a schematic view of one embodiment of an electrical stimulation system, according to the invention.
Figure 2:
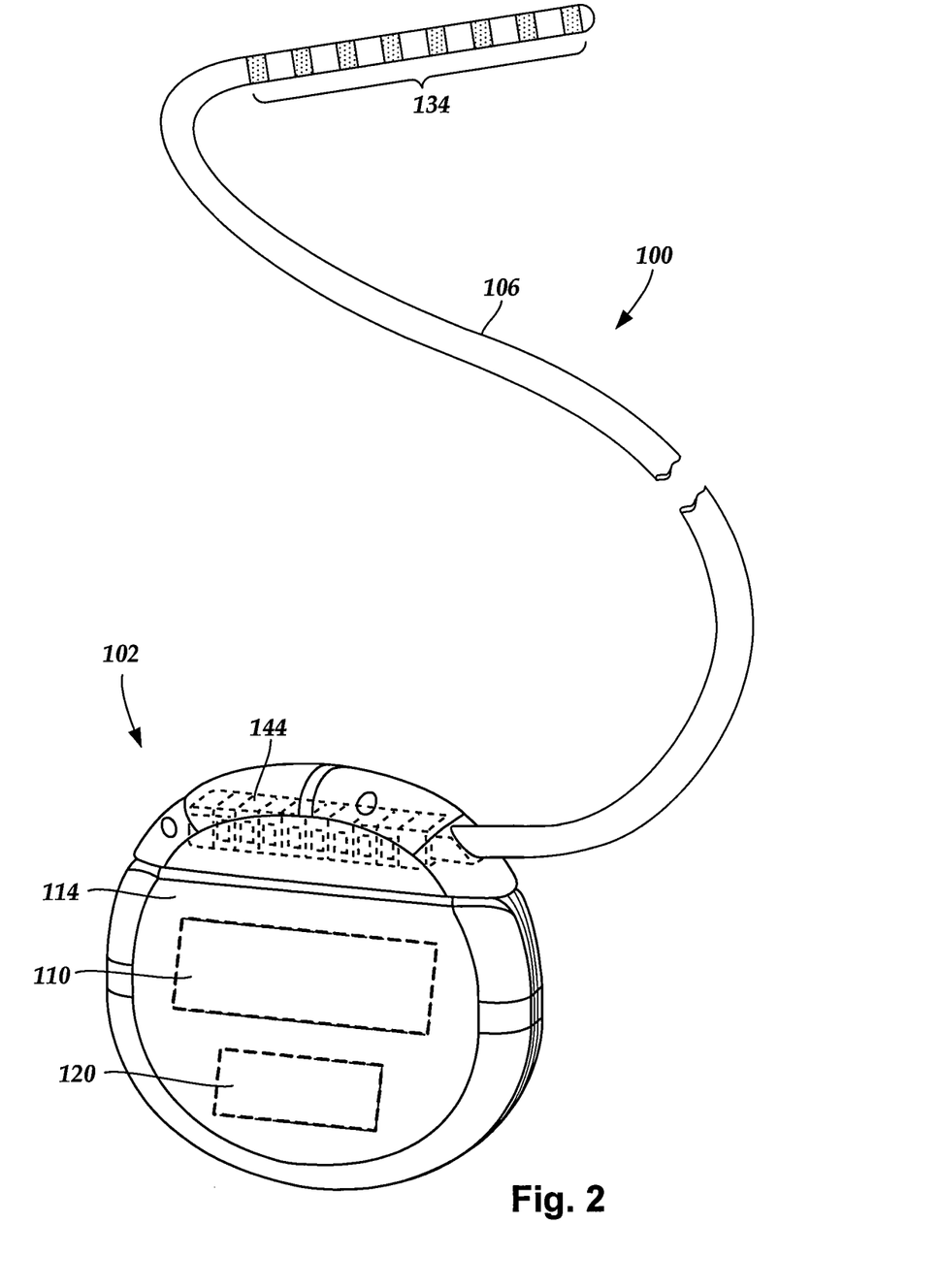
FIG. 2 is a schematic view of another embodiment of an electrical stimulation system, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the lead bodies 106 form a lead. FIG. 1 shows the electrical stimulation system comprising two lead bodies 106. However, in at least some embodiments the electrical stimulation system 100 may include only a single lead body 106 (see e.g., FIG. 2). In at least some other embodiments, the electrical stimulation system includes more than two lead bodies 106. The paddle body 104 typically includes an array of electrodes 134. The control module 102 typically includes an electronic subassembly 110 and an optional power source 120 disposed in a sealed housing 114. The control module 102 typically includes a connector 144 (FIG. 2 and 3A, see also 322 and 350 of FIG. 3B) into which the proximal end of the one or more lead bodies 106 can be plugged to make an electrical connection via aperture contacts on the control module 102 and terminals (e.g., 310 in FIG. 3A and 336 of FIG. 3B) on each of the one or more lead bodies 106. It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead. In addition, one or more lead extensions 312 (see FIG. 3B) can be disposed between the one or more lead bodies 106 and the control module 102 to extend the distance between the one or more lead bodies 106 and the control module 102 of the embodiments shown in FIGS. 1 and 2.

The electrical stimulation system or components of the electrical stimulation system, including the lead bodies 106, the paddle body 104, and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. The number of electrodes 134 in the array of electrodes 134 may vary. For example, there can be two, four, six, eight, ten, twelve, fourteen, sixteen, or more electrodes 134. As will be recognized, other numbers of electrodes 134 may also be used.

The electrodes of the paddle body 104 or one or more lead bodies 106 are typically disposed in, or separated by, a non-conductive, biocompatible material including, for example, silicone, polyurethane, polyetheretherketone ("PEEK"), epoxy, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIG. 3A and 336 of FIG. 3B) are typically disposed at the proximal end of the one or more lead bodies 106 for connection to corresponding contacts (e.g., 314 in FIG. 3A and 340 of FIG. 3B) in connectors (e.g., 144 in FIGS. 1-3A and 322 and 350 of FIG. 3B) disposed on, for example, the control module 102 (or to other devices, such as contacts on a lead extension, an operating room cable, or an adaptor). Conductive wires ("conductors") (not shown) extend from the terminals (e.g., 310 in FIG. 3A and 336 of FIG. 3B) to the electrodes 134. Typically, one or more electrodes 134 are electrically coupled to a terminal (e.g., 310 in FIG. 3A and 336 of FIG. 3B). In some embodiments, each terminal (e.g., 310 in FIG. 3A and 336 of FIG. 3B) is only connected to one electrode 134. The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

Figure 3A:
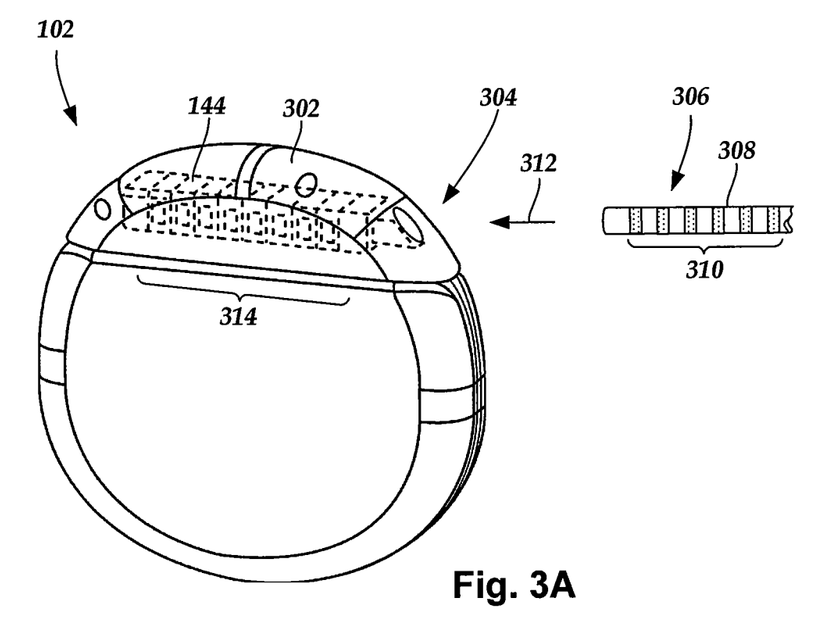
FIG. 3A is a schematic view of one embodiment of a proximal portion of a lead and a control module of an electrical stimulation system, according to the invention.

In at least some embodiments, leads are coupled to connectors disposed on control modules. In FIG. 3A, a lead 308 is shown configured and arranged for insertion into the control module 102. The connector 144 includes a connector housing 302. The connector housing 302 defines at least one port 304 into which a proximal end 306 of a lead 308 with terminals 310 can be inserted, as shown by directional arrow 312. The connector housing 302 also includes a plurality of contacts 314 for each port 304. When the lead 308 is inserted into the port 304, the contacts 314 can be aligned with the terminals 310 on the lead 308 to electrically couple the control module 102 to the electrodes (134 of FIG. 1) disposed at a distal end of the lead 308. Examples of connectors in control modules are found in, for example, U.S. Pat. No. 7,244,150 and U.S. patent application Ser. No. 11/532,844, which are incorporated herein by reference.

Figure 3B:
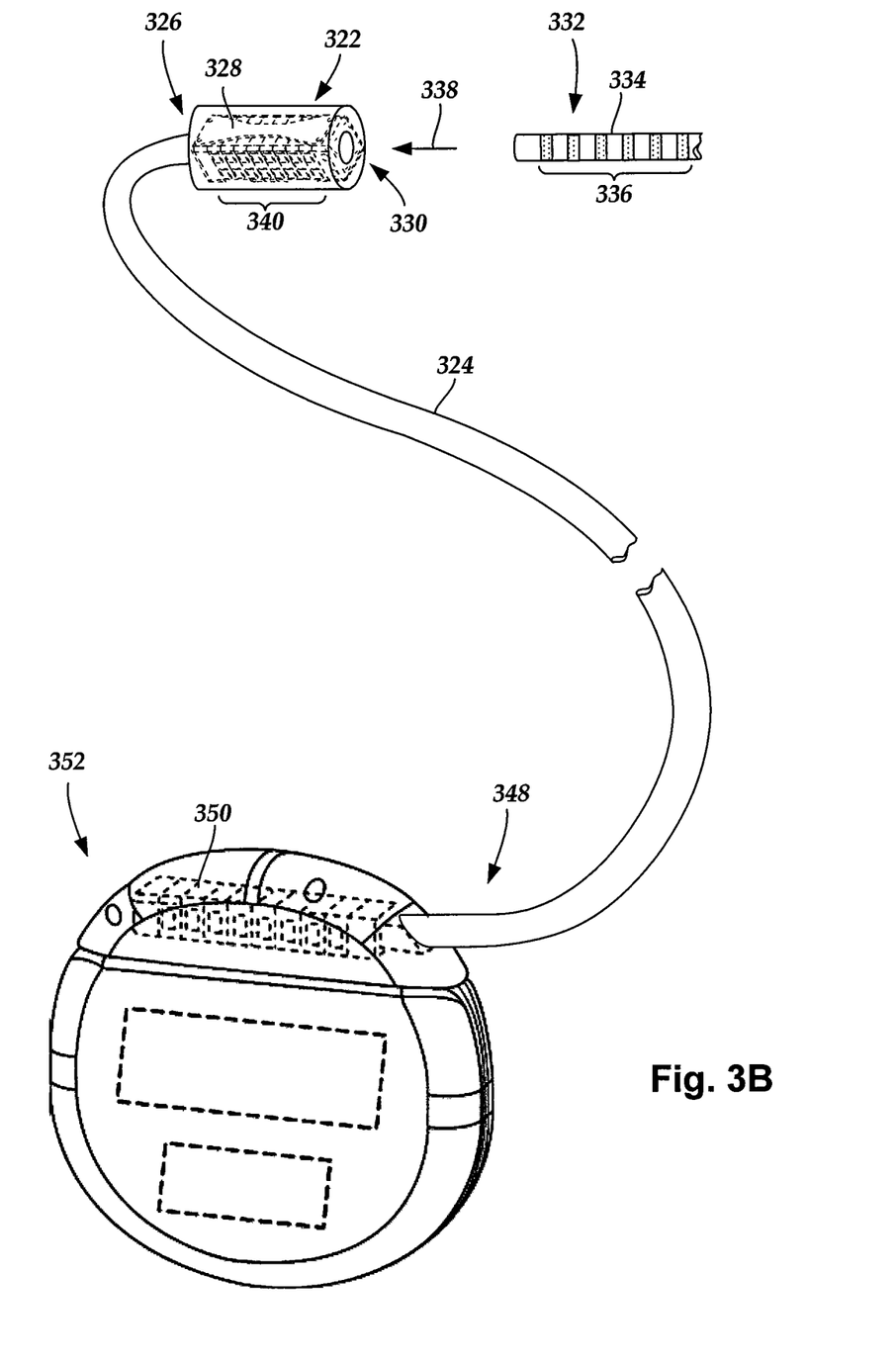
FIG. 3B is a schematic view of one embodiment of a proximal portion of a lead and a lead extension of an electrical stimulation system, according to the invention.

In FIG. 3B, a connector 322 is disposed on a lead extension 324. The connector 322 is shown disposed at a distal end 326 of the lead extension 324. The connector 322 includes a connector housing 328. The connector housing 328 defines at least one port 330 into which a proximal end 332 of a lead 334 with terminals 336 can be inserted, as shown by directional arrow 338. The connector housing 328 also includes a plurality of contacts 340. When the lead 334 is inserted into the port 330, the contacts 340 disposed in the connector housing 328 can be aligned with the terminals 336 on the lead 334 to electrically couple the lead extension 324 to the electrodes (134 of FIG. 1) disposed at a distal end (not shown) of the lead 334.

In at least some embodiments, the proximal end of a lead extension is similarly configured and arranged as a proximal end of a lead. The lead extension 324 may include a plurality of conductive wires (not shown) that electrically couple the contacts 340 to a proximal end 348 of the lead extension 324 that is opposite to the distal end 326. In at least some embodiments, the conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a connector disposed in another lead extension. In other embodiments, the proximal end 348 of the lead extension 324 is configured and arranged for insertion into a connector disposed in a control module. As an example, in FIG. 3B the proximal end 348 of the lead extension 324 is inserted into a connector 350 disposed in a control module 352.

It is important to form a connector with contacts that consistently align with terminals of an elongated member, such as a lead or lead extension, when the elongated member is inserted into a port of the connector. In at least some designs, the conductor contacts may not be evenly spaced from one another along a length of the connector. In some instances, uneven contact spacing may cause ineffective, or even inappropriate electrical connection between the contacts and terminals of inserted elongated members. For example, the contacts may be spaced such that two or more contacts electrically couple with an individual terminal of an inserted elongated member, while another terminal does not electrically couple to any of the contacts, and instead contacts an isolation seal positioned between adjacent contacts.

In some designs, one or more of the contacts may not align along a transverse axis of a connector. For example, when looking at the connector from one end, not all of the contacts align with an opening of a port of the connector. In other words, the concentricity of one or more of the contacts (or one or more isolation seals) may not be consistent. When the contacts are not all concentrically aligned with the opening of the port, an excessive amount of force may be needed to insert or remove the proximal end of the lead or lead extension from a connector. In some cases, complete insertion or removal of the proximal end of the lead or lead extension may not be achievable without damaging the connector or the proximal end of the lead or lead extension.

In at least some embodiments, a connector includes an assembly of individual contact modules arranged along a common axis. In at least some embodiments, employing an assembly of individual contact modules arranged along a common axis may improve the spacing and concentricity of aperture contacts disposed in the connector. In at least some embodiments, the connectors may be disposed in a control module (e.g., connector 144 in FIGS. 1-3A). In at least some embodiments, the connectors may be disposed on one end of an elongate member, such as the distal end of a lead extension (e.g., connector 322 in FIG. 3B).

The connector may define a single port (e.g., the connectors of FIGS. 2-3B), or the connector may define multiple ports (e.g., the connector of FIG. 1). Multi-port connectors may define any suitable number of ports including, for example, one, two, three, four, five, six, seven, eight, or more ports. As will be recognized, other numbers of ports may be defined by the connector.

Figure 4A:
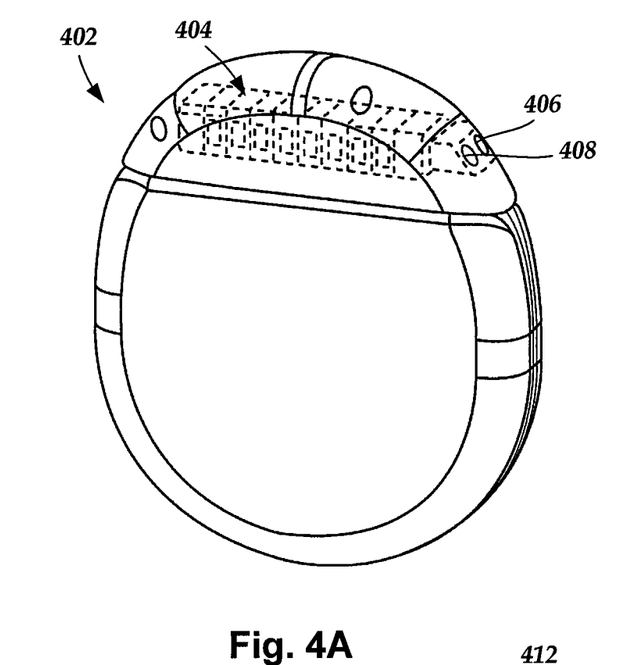
FIG. 4A is a schematic perspective view of one embodiment of a control module for an electrical stimulation system, the control module having a connector that includes an assembly of individual contact modules arranged along a common axis, the connector including two ports and sixteen aperture contacts, according to the invention.
Figure 4B:
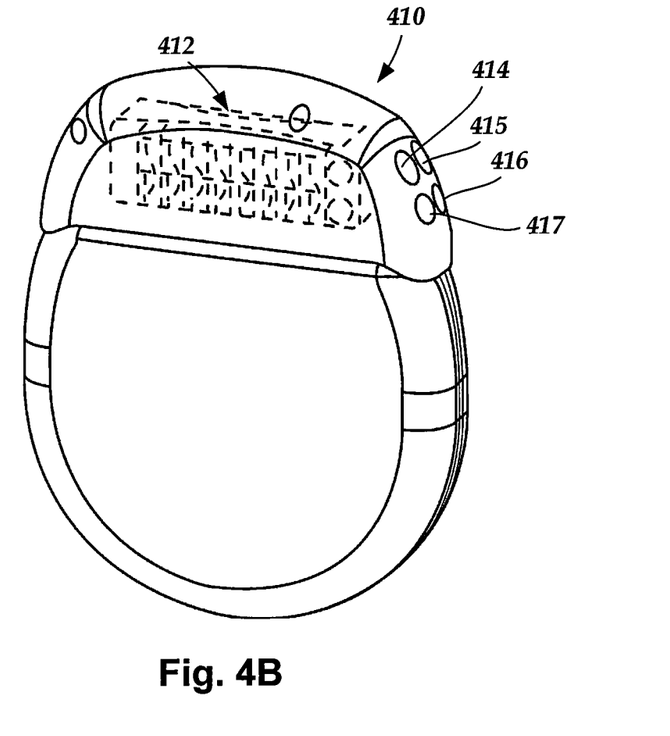
FIG. 4B is a schematic perspective view of another embodiment of a control module for an electrical stimulation system, the control module having a connector that includes an assembly of individual contact modules arranged along a common axis, the connector including four ports and thirty-two aperture contacts, according to the invention.
Figure 5:
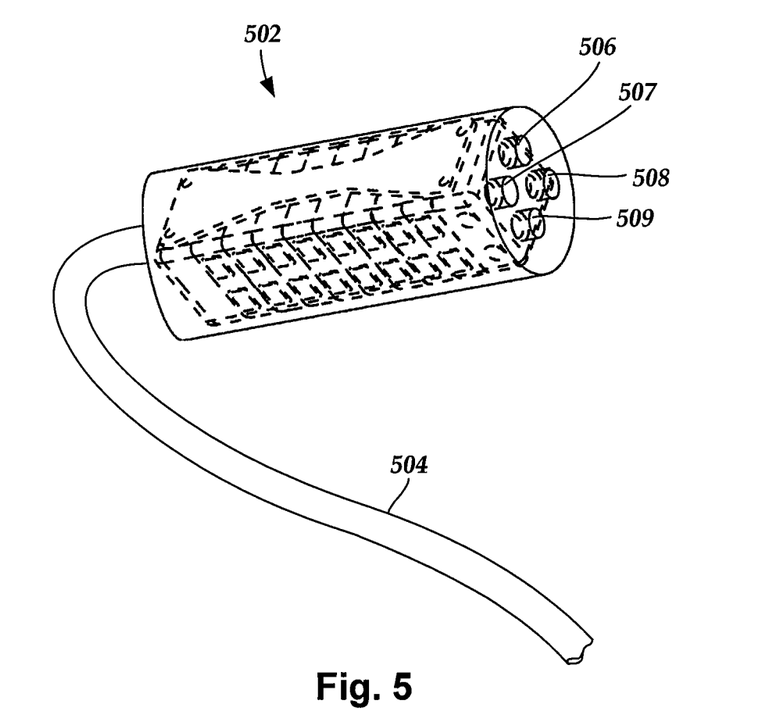
FIG. 5 is a schematic perspective view of one embodiment of a distal portion of a lead extension for an electrical stimulation system, the distal end of the lead extension having a connector that includes an assembly of individual contact modules arranged along a common axis, the connector including four ports and thirty-two aperture contacts, according to the invention.

FIG. 4A is a schematic perspective view of another embodiment of a multi-port control module 402 for an electrical stimulation system. The control module 402 includes a connector 404 defining two ports 406 and 408. FIG. 4B is a schematic perspective view of another embodiment of a control module 410. The control module 410 includes a connector 412 that defines four ports 414-417. FIG. 5 is a schematic perspective view of one embodiment of a connector 502 disposed at a distal portion of a lead extension 504. The connector 502 defines four ports 506-509.

Figure 6A:
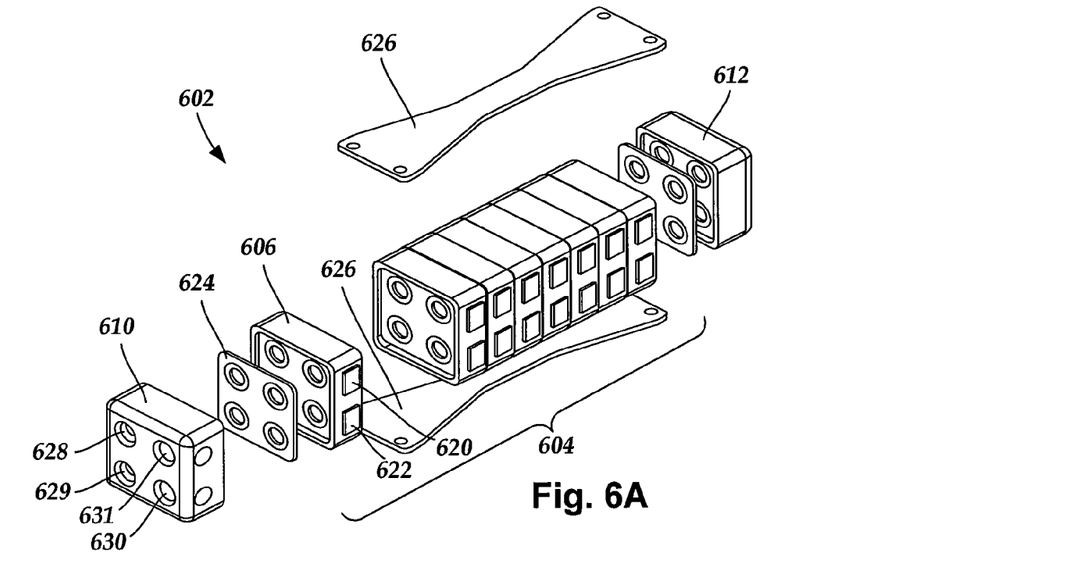
FIG. 6A is a schematic perspective exploded view of one embodiment of a connector for an electrical stimulation system, the connector including an assembly of individual contact modules sandwiched between a first end plate and a second end plate, according to the invention.
Figure 6B:
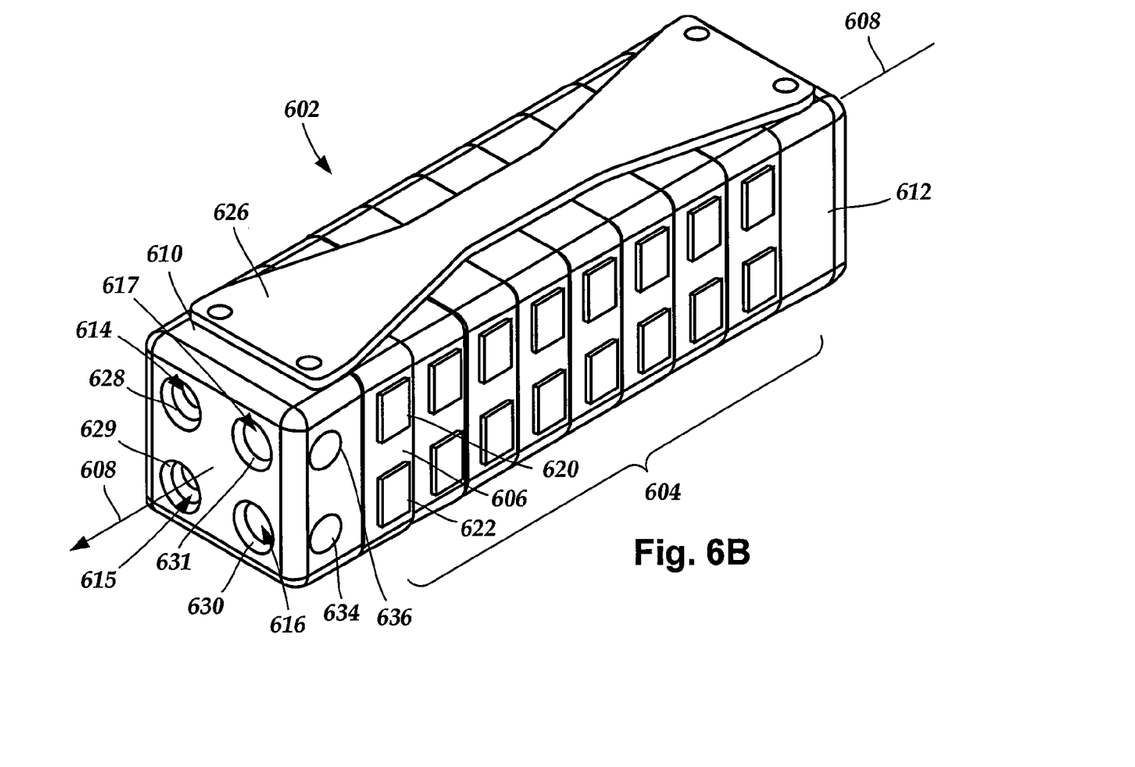
FIG. 6B is a schematic perspective view of one embodiment of a connector for an electrical stimulation system, the connector including an assembly of individual contact modules sandwiched between a first end plate and a second end plate, according to the invention.

In at least some embodiments, the connector includes end plates flanking the assembly of individual contact modules arranged along a common axis. FIGS. 6A-6B are schematic perspective views of one embodiment of a connector 602 for an electrical stimulation system. FIG. 6A is a schematic perspective exploded view of the connector 602. FIG. 6B is a schematic perspective view of the connector 602 in an assembled configuration. The connector 602 includes an assembly 604 of individual contact modules, such as contact module 606 (see e.g., 702 of FIGS. 7A-7B), arranged along a common axis 608 and sandwiched between a first end plate 610 and a second end plate 612. The connector 602 defines ports 614-617. The ports 614-617 are formed from aligned insertion apertures (see e.g., 714-717 of FIGS. 7A-7B) defined in the contact modules, such as contact module 606. Each contact module in the assembly 604 includes one or more aperture contacts, such as aperture contacts 620 and 622, disposed on contact module 606 and extending from the insertion apertures. Seal plates, such as seal plate 624, are disposed between adjacent contact modules. In at least some embodiments, the seal plates 624 are disposed between contact modules and the end plates 610 and 612.

In at least some embodiments, the number of aperture contacts disposed on each contact module is equal to the number of ports defined in the connector 602. For example, in FIGS. 6A-6B, four ports 614-617 are shown. Thus, in FIGS. 6A-6B there are four aperture contacts, two of which (620 and 622 are shown in FIGS. 6A-6B) and two of which are not shown in FIGS. 6A-6B.

In at least some embodiments, the total number of aperture contacts disposed in the connector 602 is equal to the number of contact modules in the assembly 604 multiplied by the number of ports in the connector 602. For example, in FIGS. 6A-6B, the number of contact modules in the assembly 604 is equal to eight and the number of ports in the connector 602 is equal to four. Thus, there are four aperture contacts on each contact module 606 and thirty-two aperture contacts in the assembly 604.

In at least some embodiments, the connector 602 may also include one or more retention mechanisms, such as retention mechanism 626, for maintaining the assembly 604 of individual contact modules arranged along the common axis 608. In at least some embodiments, the one or more retention mechanisms 626 couple the end plates 610 and 612 together and hold the contact modules in place by squeezing the contact modules 604 between the end plates 610 and 612. In at least some embodiments, the one or more retention mechanisms 626 include a longitudinal length with at least one planar surface against which the contact modules of the assembly 604 (such as the contact module 606) may press against to align the contact modules of the assembly 604 with one another.

In at least some embodiments, either or both of the end plates 610 and 612 may include one or more insertion apertures which define the ingress of the one or more ports defined in the connector. In FIGS. 6A-6B, the end plate 610 defines the insertion apertures 628-631 which define the ingress of the ports 614-617, respectively. Thus, one or more elongated members are inserted from the first end plate 610. In at least some other embodiments, one or more ports open from the second end plate 612. In at least some other embodiments, at least one port opens from the first end plate 610 and at least one port opens from the second end plate 612. In which case, elongated members may be inserted from either of the end plates 610 and 612, depending on which end plate 610 and 612 includes an ingress for a given port. In at least some embodiments, when one of the end plates 610 and 612 defines an ingress to a port, the other of the end plates 610 and 612 includes a stop to aid with proper insertion of an elongated member into the port to facilitate proper alignment between terminals on the elongated member and aperture contacts disposed in the contact modules of the assembly 604.

In at least some embodiments, one or more fasteners may be employed to retain one or more inserted elongated members in ports 614-617 of the connector 602. Any suitable fastener may be used to retain one or more elongated members in ports 614-617. In FIGS. 6A-6B, fastener apertures 634 and 636 are shown which are positioned to retain elongated members inserted in ports 616 and 617, respectively. Thus, in at least some embodiments, a fastener (e.g., a set screw and the like) may be inserted into the fastener apertures 616 and 617 and tightened against an inserted elongated member.

The connector 602 may include any suitable number of contact modules (such as contact module 606) in the assembly 604 including, for example, one, two, three, four, five, six, seven, eight, nine, ten, twelve, sixteen, twenty, twenty-four, thirty-two, or more contact modules. As will be recognized, other numbers of contact modules (such as contact module 606) may be included in the assembly 604 as well.

The contact modules of the assembly 604 may be formed from any suitable biocompatible, rigid, non-conductive material including, for example, polyurethane, PEEK, polysulphone, silicone, epoxy, and the like or combinations thereof.

The contact modules of the assembly 604 may be formed in any suitable transverse cross-sectional shape for disposing in the connector housing (e.g., on a control module, on a lead extension, or the like) including, for example, round, oval, triangular, rectangular, pentagonal, hexagonal, heptagonal, octagonal, nonagonal, decagonal, star-shaped, bell-shaped, asterisk-shaped, cruciform-shaped, and the like. The contact modules of the assembly 604 may be formed in the desired shape by any process including, for example, molding (including injection molding), casting, and the like.

Figure 7A:
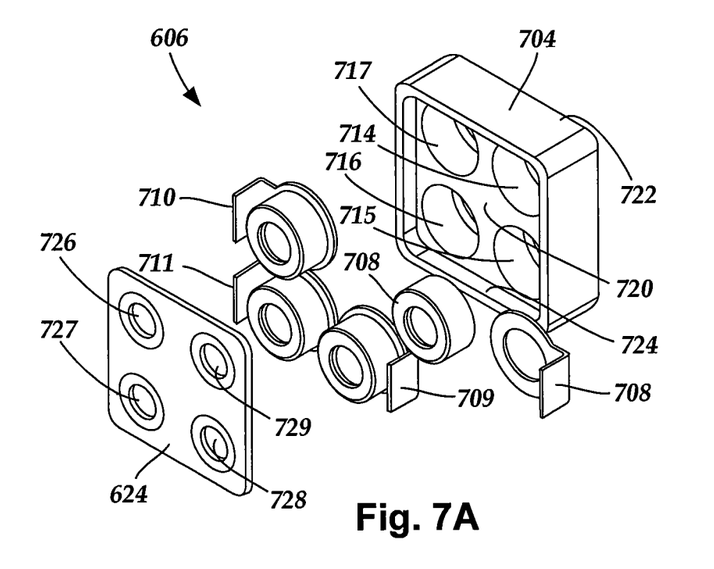
FIG. 7A is a schematic perspective exploded view of one embodiment of a seal plate coupled to an individual contact module of the connector of FIG. 6B, according to the invention.
Figure 7B:
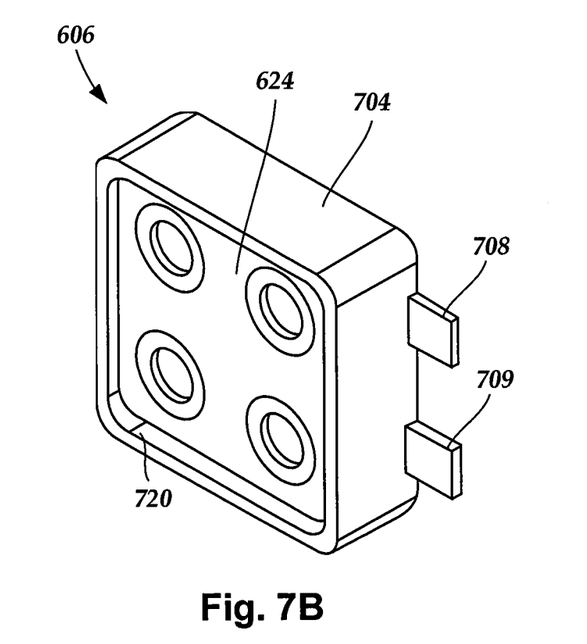
FIG. 7B is a schematic perspective view of one embodiment of a seal plate coupled to an individual contact module of the connector of FIG. 6B, according to the invention.

FIGS. 7A-7B are schematic perspective views of one embodiment of the contact module 606 and the seal plate 624 coupled to the contact module 606. FIG. 7A is a schematic perspective exploded view of the contact module 606 and the seal plate 624. FIG. 7B is a schematic perspective view of the contact module 606 and the seal plate in an assembled configuration. The contact module 606 includes a body 704 that defines a plurality of insertion apertures 714-717. The body 704 includes opposing major surfaces, such as the first major surface 720 and the second major surface 722. The insertion apertures 714-717 extend between the first major surface 720 and the second major surface 722. A plurality of aperture contacts 708-711 are disposed in the contact module 606 such that a different one of the aperture contacts 708-711 is at least partially exposed in each insertion aperture 714-717. Note that in FIG. 7B, aperture contacts 710 and 711 are obstructed from view by the body 704.

The aperture contacts 708-711 are configured and arranged to electrically couple to terminals disposed on elongated members when the elongated members are inserted into the corresponding ports 614-617. In at least some embodiments, the aperture contacts 708-711 are electrically coupled to the electronic subassembly (110 in FIG. 1) of the control module (see e.g., 102 in FIG. 1). The aperture contacts 708-711 may contact inserted terminals of elongated members using any suitable contact mechanism, such as a compression fit, a conductor-to-conductor contact mechanism, for example, a coiled spring, a leaf spring, a compression spoon, a set screw, a ring, and the like or combinations thereof.

In at least some embodiments, the body 704 includes one or more guide features configured and arranged to facilitate alignment and stacking of multiple contact modules along a common axis. For example, one or more protruding guide features may be disposed along at least a portion of the first surface 720 of the body 704 that are configured and arranged to mate with corresponding depression guide features in the second major surface 722 of an adjacent contact module (or an end plate).

The aperture contacts 708-711 may be formed from any suitable biocompatible, inert, conductive material including, for example, platinum, platinum/Iridium, niobium, titanium, palladium, stainless steel (e.g., 316L, BioDur® 316LS, Bio-Dur® 108), MP35N, as well as alloys of the abovementioned, and the like or combinations thereof.

The aperture contacts 708-711 may be formed in the desired shape by any process including, for example, molding (including injection molding), casting, and the like. In at least some embodiments, aperture contacts are insert-molded into the contact module 604. In other embodiments, the aperture contacts are inserted into the contact modules, such as the contact module 606, after the bodies of the contact modules are formed.

The seal plate 624 electrically isolates each of the aperture contacts 708-711 disposed in the contact module 606 from each other and also from aperture contacts disposed on adjacent contact modules when the contact module 606 is stacked with other contact modules to form an assembly (see e.g., assembly 604). The seal plate 624 may be either removably or permanently coupled to the body 704. In at least some embodiments, the body 704 includes a seat 724 into which the seal plate 624 is disposed. In at least some embodiments, the seal plate 624 is disposed in the seat 724 such that the seal plate 624 does not extend beyond the plane of the body 704.

In at least some embodiments, the seal plate 624 defines insertion apertures 726-729 that align with the insertion apertures 714-717 of the contact module 606. In at least some embodiments, the insertion apertures 714-717 of the contact module 606 and the insertion apertures 726-729 of the seal plate 624 are positioned such that, when the connector 602 is assembled, the insertion apertures 714-717 of the contact module 606 and the insertion apertures 726-729 of the seal plate 624 align with similarly-positioned insertion apertures defined in one or more of the end plates (e.g., the insertion apertures 628-631 of the end plate 610).

Figure 8:
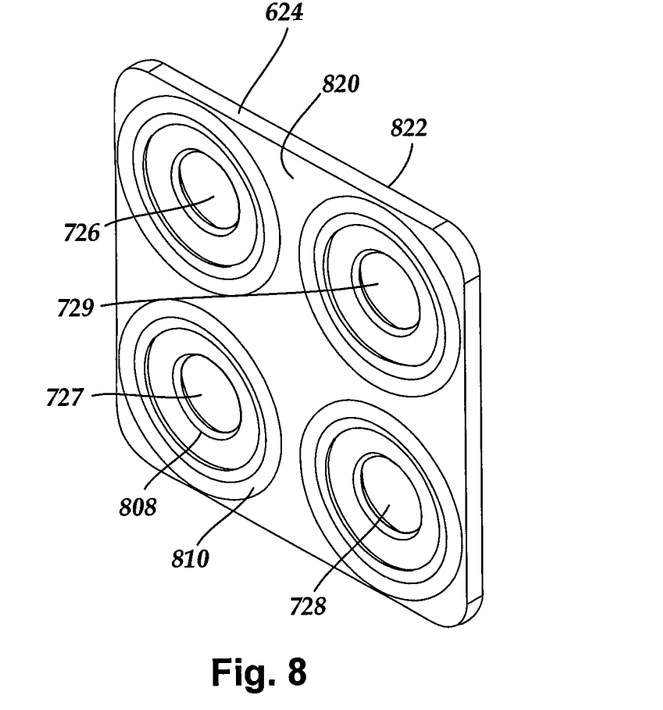
FIG. 8 is a schematic perspective view of one embodiment of the seal plate of FIG. 7, according to the invention.

FIG. 8 is a schematic perspective view of one embodiment of the seal plate 624. In at least some embodiments, the seal plate 624 is configured and arranged to isolate each of the aperture contacts disposed in contact modules from other aperture contacts, either disposed on the same contact module, or disposed on other contact modules of the assembly (see e.g., assembly 604). In at least some embodiments, the seal plate 624 includes opposing major surfaces, such as the first major surface 820 and the second major surface 822. The insertion apertures 726-729 extend between the first major surface 820 and the second major surface 822.

The seal plate 624 is formed, preferably, from a non-conductive material suitable for implantation including, for example, polyurethane, PEEK, polysulphone, silicone, epoxy, and the like or combinations thereof.

In at least some embodiments, each insertion aperture 726-729 is encircled by one or more seals. In at least some embodiments, the one or more seals encircle a given insertion aperture of the seal plate 624 and provide a fluidtight seal around the aperture contact disposed in proximity to the insertion aperture.

The one or more seals may be formed from any suitable biocompatible, pliable, non-conductive material including, for example, silicone, a thermoplastic elastomer, and the like. The one or more seals may be formed as any suitable type of seal including, for example, a flat blade seal, a radial seal, or the like. The one or more seals may be coupled to the seal plate 706 in any suitable manner including, for example, insert-molding the one or more seals into the seal plate 624 or coupling the one or more seals into the seal plate 624 after the seal plate 624 is formed.

FIG. 8 shows each insertion aperture 726-729 encircled by a first seal 808 and a second seal 810. In at least some embodiments, the first seal 808 is configured and arranged for electrically isolating the aperture contacts disposed on the same contact module (702 in FIGS. 7A-7B) from one another. For example, in at least some embodiments, the first seal 808 may be used to electrically isolate the aperture contact (710 in FIGS. 7A-7B) from the remaining aperture contacts (708, 709, and 711 of FIGS. 7A-7B) on the contact module (606 in FIGS. 7A-7B).

In at least some embodiments, the second seal is configured and arranged for electrically isolating the aperture contacts disposed on the contact module (702 in FIGS. 7A-7B) from aperture contacts disposed on an abutting contact module in the assembly (604 in FIGS. 6A-6B). For example, in at least some embodiments, the second seal 810 may be used to electrically isolate the aperture contact (710 in FIGS. 7A-7B) from a similarly-positioned aperture contact disposed on a conductor element positioned adjacent to the contact module (702 in FIGS. 7A-7B) in the assembly (604 in FIGS. 6A-6B).

In at least some embodiments, the seal plate 624 includes the first seal 808, but not the second seal 810. In at least some embodiments, the seal plate 624 includes the second seal 810, but not the first seal 808. In at least some embodiments, the seal plate 624 includes both the first seal 808 and the second seal 810.

Figure 9:
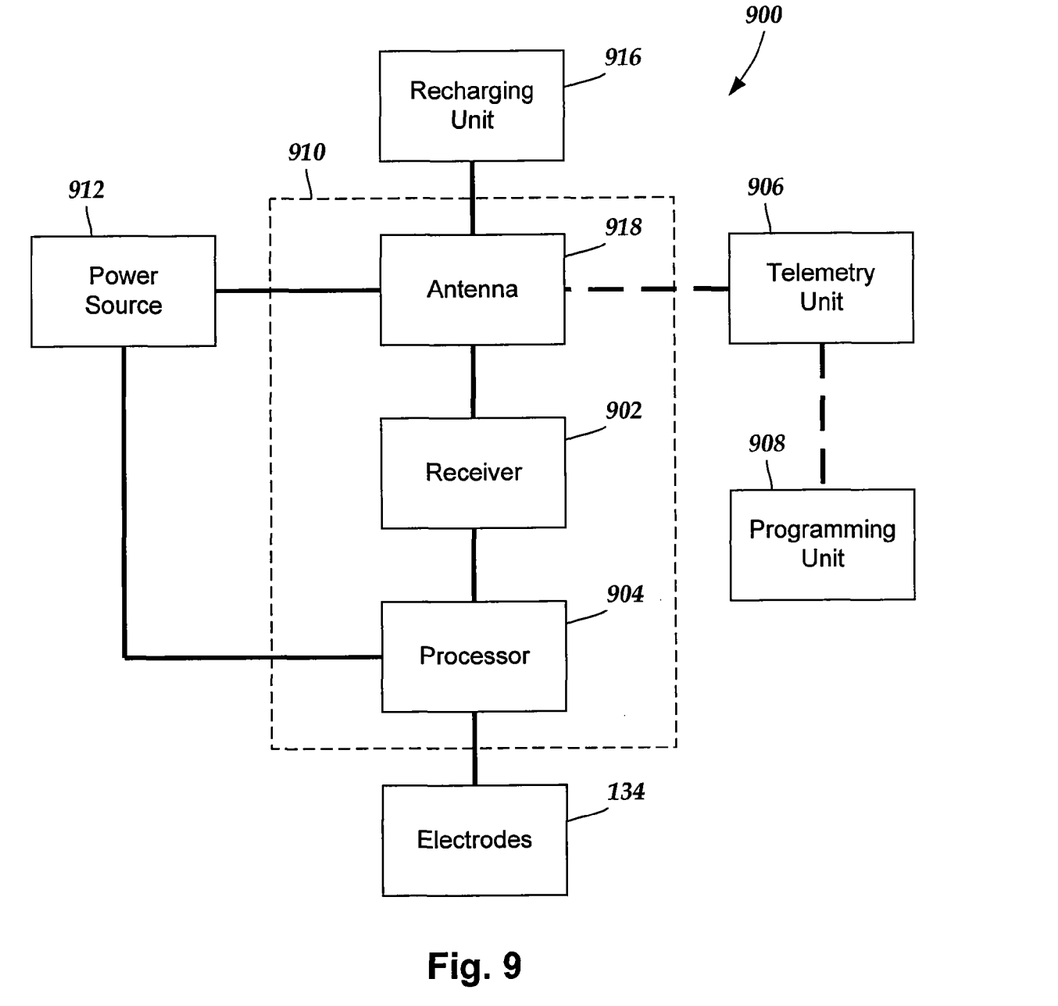
FIG. 9 is a schematic overview of one embodiment of components of a stimulation system, including an electronic subassembly disposed within a control module, according to the invention.

FIG. 9 is a schematic overview of one embodiment of components of an electrical stimulation system 900 including an electronic subassembly 910 disposed within a control module. It will be understood that the electrical stimulation system can include more, fewer, or different components and can have a variety of different configurations including those configurations disclosed in the stimulator references cited herein.

Some of the components (for example, power source 912, antenna 918, receiver 902, and processor 904) of the electrical stimulation system can be positioned on one or more circuit boards or similar carriers within a sealed housing of an implantable pulse generator, if desired. Any power source 912 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Patent Application Publication No. 2004/0059392, incorporated herein by reference.

As another alternative, power can be supplied by an external power source through inductive coupling via the optional antenna 918 or a secondary antenna. The external power source can be in a device that is mounted on the skin of the user or in a unit that is provided near the user on a permanent or periodic basis.

If the power source 912 is a rechargeable battery, the battery may be recharged using the optional antenna 918, if desired. Power can be provided to the battery for recharging by inductively coupling the battery through the antenna to a recharging unit 916 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 904 is generally included to control the timing and electrical characteristics of the electrical stimulation system. For example, the processor 904 can, if desired, control one or more of the timing, frequency, strength, duration, and waveform of the pulses. In addition, the processor 904 can select which electrodes can be used to provide stimulation, if desired. In some embodiments, the processor 904 may select which electrode(s) are cathodes and which electrode(s) are anodes. In some embodiments, the processor 904 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 908 that, for example, allows modification of pulse characteristics. In the illustrated embodiment, the processor 904 is coupled to a receiver 902 which, in turn, is coupled to the optional antenna 918. This allows the processor 904 to receive instructions from an external source to, for example, direct the pulse characteristics and the selection of electrodes, if desired.

In one embodiment, the antenna 918 is capable of receiving signals (e.g., RF signals) from an external telemetry unit 906 which is programmed by a programming unit 908. The programming unit 908 can be external to, or part of, the telemetry unit 906. The telemetry unit 906 can be a device that is worn on the skin of the user or can be carried by the user and can have a form similar to a pager, cellular phone, or remote control, if desired. As another alternative, the telemetry unit 906 may not be worn or carried by the user but may only be available at a home station or at a clinician's office. The programming unit 908 can be any unit that can provide information to the telemetry unit 906 for transmission to the electrical stimulation system 900. The programming unit 908 can be part of the telemetry unit 906 or can provide signals or information to the telemetry unit 906 via a wireless or wired connection. One example of a suitable programming unit is a computer operated by the user or clinician to send signals to the telemetry unit 906.

The signals sent to the processor 904 via the antenna 918 and receiver 902 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 900 to cease operation, to start operation, to start charging the battery, or to stop charging the battery. In other embodiments, the stimulation system does not include an antenna 918 or receiver 902 and the processor 904 operates as programmed.

Optionally, the electrical stimulation system 900 may include a transmitter (not shown) coupled to the processor 904 and the antenna 918 for transmitting signals back to the telemetry unit 906 or another unit capable of receiving the signals. For example, the electrical stimulation system 900 may transmit signals indicating whether the electrical stimulation system 900 is operating properly or not or indicating when the battery needs to be charged or the level of charge remaining in the battery. The processor 904 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A connector for an electrical stimulation system, the connector comprising:

an assembly of individual contact modules arranged along a common axis, the assembly having a first end, an opposing second end, and a longitudinal outer surface extending along the common axis between the first end and the second end, the longitudinal outer surface having a rectangular cross-section that comprises four flat sides, each contact module comprising a body having a first major surface, an opposing second major surface, and four flat edges extending between the first major surface and the second major surface, the four flat edges forming a portion of the longitudinal outer surface of the assembly, the first major surface defining a seat and at least two insertion apertures, the body comprising at least two aperture contacts, each aperture contact being associated with one of the insertion apertures, wherein each of the aperture contacts forms a closed loop of electrically conductive material configured and arranged to electrically couple to a terminal of an elongated member when the elongated member is inserted into the associated insertion aperture;

a first end plate positioned at the first end of the assembly of individual contact modules;

a plurality of seal plates, a different one of the plurality of seal plates being disposed in the seat of an associated one of the contact modules such that the seal plate is sandwiched between the associated contact module and one other contact module of the assembly or the first end plate, wherein each seal plate is configured and arranged to electrically isolate the aperture contacts of the associated contact module from the aperture contacts of the other contact modules; and a second end plate positioned at the second end of the assembly of individual contact modules, the second end plate coupled to the first end plate by a retaining mechanism and configured and arranged to facilitate arrangement of the assembly along the common axis;

wherein the retaining mechanism comprises at least one planar surface configured and arranged to lay flat over a plane formed by one of the four flat sides of the longitudinal outer surface of the assembly.

2. The connector of claim 1, wherein each seal plate is removably disposed in the seat defined in the first major surface.

3. The connector of claim 1, wherein each seal plate is permanently disposed in the seat defined in the first major surface.

4. The connector of claim 1, wherein each seal plate defines at least two insertion apertures, the at least two insertion apertures of the seal plate aligning with the at least two insertion apertures of the contact module on which the seal plate is disposed.

5. The connector of claim 1, wherein for each seal plate the at least two insertion apertures defined in the seal plate are each encircled by at least one seal, the at least one seal configured and arranged to electrically isolate the aperture contact around which the at least one seal is disposed.

6. The connector of claim 5, wherein the at least one seal is a blade seal or a radial seal.

7. The connector of claim 1, wherein the first end plate defines at least two insertion apertures aligned with the at least two insertion apertures defined for the contact modules of the assembly.

8. The connector of claim 1, wherein each contact module comprises at least one guiding feature configured and arranged to facilitate arrangement of the contact modules along the common axis.

9. The connector of claim 1, wherein the first end plate defines a first insertion aperture aligned with one of the at least two insertion apertures, and wherein the second end plate defines a second insertion aperture aligned with a different one of the at least two insertion apertures.

10. A medical device comprising:
the connector of claim 1; and
at least one elongated member, each of the at least one elongated member having a distal end and a proximal end, each of the at least one elongated members comprising
a plurality of electrodes disposed on the distal end,
a plurality of terminals disposed on the proximal end,
a plurality of conductors, each conductor electrically coupling at least one of the electrodes to at least one of the terminals;
wherein the at least one elongated member is configured and arranged for insertion into the connector.

11. An electrical stimulating system comprising:
a control module configured and arranged to electrically couple to at least one medical lead, the control module comprising
a housing,
the connector of claim 1 coupled to the housing, and
an electronic subassembly disposed in the housing and electrically coupled to the connector.

12. A connector for an electrical stimulation system, the connector comprising:
an assembly of individual contact modules arranged along a common axis, the assembly having a first end, an opposing second end, and a longitudinal outer surface extending along the common axis between the first end and the second end, the longitudinal outer surface having a rectangular cross-section that comprises four flat sides, each contact module comprising
a body defining at least two insertion apertures, the body having a first major surface, an opposing second major surface, and four flat edges extending between the first major surface and the second major surface, the four flat edges forming a portion of the longitudinal outer surface of the assembly, and
for each of the at least two insertion apertures, an aperture contact is disposed in the body and exposed in the corresponding insertion aperture, the aperture contact forming a closed loop of electrically conductive material configured and arranged to electrically couple to a terminal of an elongated member when the elongated member is inserted into a corresponding one of the at least two insertion apertures;
a first end plate positioned at the first end of the assembly of individual contact modules, the first end plate defining at least two insertion apertures, wherein the insertion apertures of the first end plate are configured and arranged to align with the insertion apertures of each of the contact modules;
a plurality of seal plates, each seal plate coupled to the body of one of the contact modules such that each seal plate is sandwiched between the contact module onto which the seal plate is coupled and one of another contact module of the assembly or the first end plate, the seal plate defining at least two insertion apertures, wherein each seal plate is configured and arranged to electrically isolate each of the aperture contacts from other aperture contacts in an adjacent contact module;
a second end plate positioned at the second end of the assembly of individual contact modules; and
at least one retaining mechanism configured and arranged to maintain each of the individual contact modules arranged along the common axis, the at least one retaining mechanism coupled to at least one of the first end plate or the second end plate, wherein the retaining mechanism comprises at least one planar surface configured and arranged to lay flat over a plane formed by one of the four flat sides of the longitudinal outer surface of the assembly.

13. The connector of claim 12, wherein the connector defines at least two ports, each port defined by one of the at least two insertion apertures of the first end plate, one of the at least two insertion apertures of each of the contact modules, and one of the at least two insertion apertures of each of the seal plates.

14. The connector of claim 12, wherein at least one seal is disposed around each of the at least two insertion apertures of the seal plate, the at least one seal configured and arranged to further electrically isolate the aperture contact disposed in proximity to the aperture contact around which the at least one seal is disposed from other aperture contacts.

15. The connector of claim 12, wherein the number of aperture contacts disposed in the connector is equal to the number of the insertion apertures defined in each of the contact modules multiplied by the number of contact modules of the assembly.

16. A medical device comprising:
the connector of claim 12; and
at least one elongated member, each of the at least one elongated member having a distal end and a proximal end, each of the at least one elongated members comprising
a plurality of electrodes disposed on the distal end,
a plurality of terminals disposed on the proximal end, and
a plurality of conductors, each conductor electrically coupling at least one of the electrodes to at least one of the terminals;
wherein the at least one elongated member is configured and arranged for insertion into the connector.

17. An electrical stimulating system comprising:
a control module configured and arranged to electrically couple to at least one medical device, the control module comprising
a housing,
the connector of claim 12 coupled to the housing, and
an electronic subassembly disposed in the housing and electrically coupled to the connector.

18. A method for forming a connector, the method comprising:
inserting a seal plate into a seat defined in a contact module for each of a plurality of contact modules, the contact module defining at least two insertion apertures, the seal plate defining at least two insertion apertures aligned with the at least two insertion apertures defined in each contact module, the seal plate comprising at least one seal disposed around each insertion aperture defined in the seal plate, the contact module comprising an aperture contact configured and arranged to electrically couple with a terminal of an elongated member when the elongated member is inserted in the insertion aperture;

aligning the plurality of contact modules and coupled seal plates along an axis so that the insertion apertures of the plurality of contact modules are aligned; and retaining the plurality of contact modules between a first end cap at a first end of the aligned plurality of contact modules and a second end cap at a second end of the aligned plurality of contact modules, wherein the first end cap defines at least two insertion apertures aligned with the at least two insertion apertures defined in each contact module thereby forming at least two ports configured and arranged to receive an elongated member with spaced-apart terminals.

19. The method of claim 18, wherein the second end cap is configured and arranged for facilitating proper alignment of terminals of an elongated member and aperture contacts of the contact modules when the elongated member is inserted in one of the ports disposed in the contact module.

20. The method of claim 18, wherein retaining the plurality of contact modules between a first end cap at a first end of the aligned plurality of contact modules and a second end cap at a second end of the aligned plurality of contact modules comprises coupling the first end cap to the second end cap by at least one retention mechanism.

\* \* \* \* \*